United States Patent [19]

Siefering et al.

[11] Patent Number: 5,304,796
[45] Date of Patent: Apr. 19, 1994

[54] ATMOSPHERIC PRESSURE IONIZATION MASS SPECTROSCOPY METHOD INCLUDING A SILICA GEL DRYING STEP

[75] Inventors: Kevin L. Siefering, Cary; Walter H. Whitlock, Chapel Hill, both of N.C.

[73] Assignee: The BOC Group, Inc., Murray Hill, N.J.

[21] Appl. No.: 858,388

[22] Filed: Mar. 25, 1992

[51] Int. Cl.[5] .............................................. B01D 59/44
[52] U.S. Cl. ................................... 250/282; 250/281; 250/288
[58] Field of Search .................. 250/281, 282, 288 R, 250/288 A, 423 R, 423 F; 73/31.03

[56] References Cited

U.S. PATENT DOCUMENTS

| | | | |
|---|---|---|---|
| 3,342,990 | 9/1967 | Barrington et al. | 250/281 |
| 3,649,199 | 3/1972 | Littlejohn | 250/281 |
| 4,156,653 | 5/1979 | McKnight | 250/533 |
| 4,182,656 | 1/1980 | Ahnell et al. | 435/34 |
| 4,239,967 | 12/1980 | Carr et al. | 250/288 |
| 4,888,482 | 12/1989 | Kato | 250/281 |
| 4,898,599 | 2/1990 | Settlemyer | 55/28 |
| 5,012,052 | 4/1991 | Hayes | 250/288 |
| 5,051,583 | 9/1991 | Mimura et al. | 250/288 |
| 5,095,206 | 3/1992 | Bacon, Jr. et al. | 250/282 |
| 5,214,952 | 6/1993 | Leggett et al. | 73/1 G |

Primary Examiner—Jack I. Berman
Assistant Examiner—James Beyer
Attorney, Agent, or Firm—David M. Rosenblum; Larry R. Cassett

[57] ABSTRACT

The present invention provides a method of analyzing a gas sample for trace impurity concentration by atmospheric pressure ionization mass spectroscopy. In accordance with the present invention, moisture is removed from the gas sample before analysis by passing the gas sample through a dried bed of silica gel. The bed of silica gel is sufficiently dried so that remaining moisture present in the gas sample after passage through the bed is at a sufficiently low concentration such that the trace impurity concentration as analyzed by atmospheric ionization mass spectroscopy will not be effected by the remaining moisture.

3 Claims, 1 Drawing Sheet

ATMOSPHERIC PRESSURE IONIZATION MASS SPECTROSCOPY METHOD INCLUDING A SILICA GEL DRYING STEP

BACKGROUND OF THE PRIOR ART

The present invention relates to a method of analyzing a gas for trace impurities by atmospheric pressure ionization mass spectroscopy (APIMS). More particularly, the present invention relates to such a method in which moisture is removed from the gas prior to performing the analysis.

In ultra-high purity gas distribution systems it is necessary to ensure that the ultra-high purity gas retains its purity from the point of supply to the point of delivery. This is particularly important in the semiconductor industry because impurities present in an ultra-high purity gas being used in the manufacture of semiconductors can reduce yield of finished product.

In the semiconductor industry, APIMS has arisen as a principal technique in assuring the continued purity of ultra-high purity gases by being able to measure trace impurities in parts per billion and parts per trillion. The performance of an APIMS analysis is not however problem free in that moisture levels of as low as one part per billion can introduce substantial analytical errors when an ultra-high purity gas is being analyzed for the presence of trace impurities other than moisture. The errors arise from plasma saturation effects and from interference of moisture generated ions with signals of, for instance, trace levels of oxygen, methane and carbon dioxide ions.

In the prior art of moisture removal from gases materials such as alumina, organic solvents, sieving materials and etc. have been used. These techniques are not applicable to APIMS analysis because they either remove secondary trace impurities such as carbon dioxide and oxygen or they add impurities, such as organics. In order to overcome the problem of the presence of moisture in a gas sample to be analyzed by APIMS, the effect of moisture is compensated for in the results by numerical techniques. The problem with the use of numerical techniques is that they represent mathematical approximations and as such present an inherent margin of error.

As will be discussed, the present invention provides a method of performing an APIMS analysis in which moisture is removed from the gas sample to be analyzed before conducting the analysis so that numerical techniques do not have to be utilized in interpreting the results of the analysis.

SUMMARY OF THE INVENTION

The present invention provides a method of analyzing a gas for trace impurity concentration by atmospheric pressure ionization mass spectroscopy. In accordance with the improved method, moisture is removed from the gas sample before analyzing the gas sample by passing the gas sample through a bed of silica gel. Before passing the gas sample through the bed of silica gel, the bed is sufficiently dried so that remaining moisture present in the gas sample after passage through the bed of silica gel is at a sufficiently low concentration such that the trace impurity concentration as analyzed by atmospheric pressure ionization mass spectroscopy will not be effected by the remaining moisture.

It has been found by the inventors herein that the use of silica gel is very effective in removing moisture for an APIMS analysis because it will selectively remove moisture only and not other components possibly present in the gas to be analyzed. Additionally, it has been found by the inventors herein that silica gel will allow a reduction in moisture levels to below one part per billion to allow analysis of a gas sample for trace impurities by APIMS without having to interpret the results of the analysis by numerical techniques to factor out the effect of moisture. While it has been known that silica gel removed moisture, it had not been known that silica gel could be used to remove moisture to produce the low level of moisture required for analysis by APIMS.

BRIEF DESCRIPTION OF THE DRAWINGS

While the invention concludes with claims particularly pointing out the subject matter that Applicants regards as their invention, it is believed that the invention will be more clearly understood when taken in conjunction with the accompanying sole FIGURE which comprises a schematic representation of an apparatus for carrying out a method in accordance with the present invention, including a packed silica gel bed shown in cross-section.

DETAILED DESCRIPTION OF THE INVENTION

Figure 1:
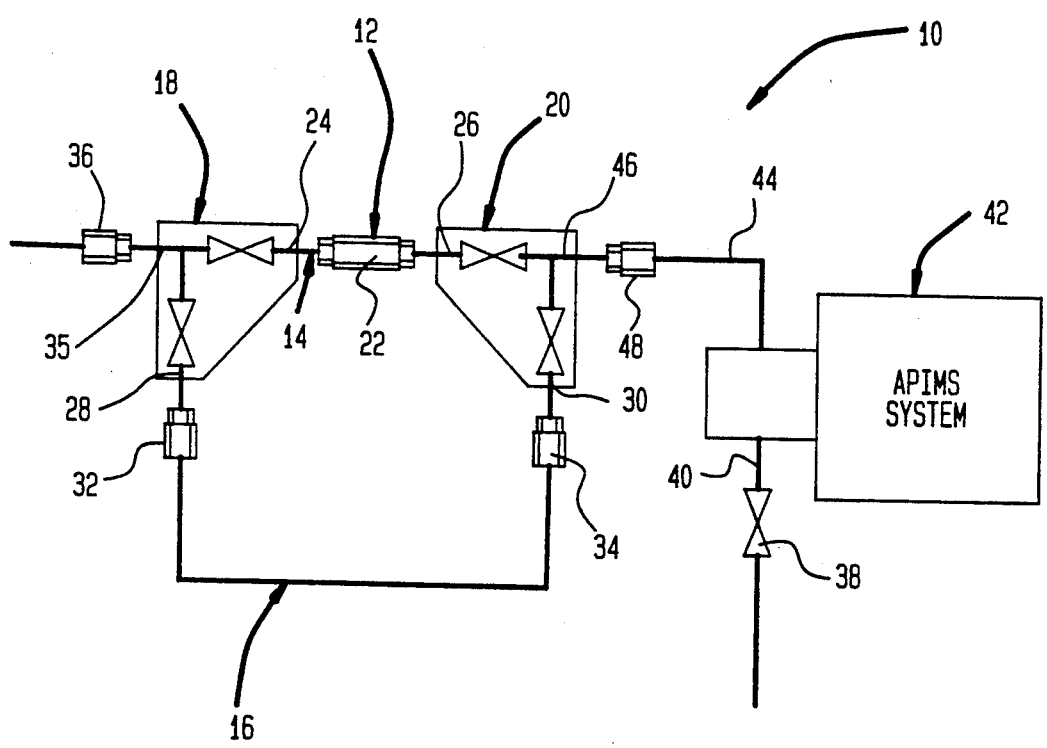

With reference to the FIGURE an apparatus 10 is illustrated for carrying out a method in accordance with the present invention. Apparatus 10 consists of a flow circuit 12 having a main flow path 14 and a branch flow path 16. Main and branch flow paths 14 and 16 are formed by connecting first and second metallic 3-way block valves 18 and 20 to one another via a face seal fitting 22 at outlet ports 24 and 26, respectively. Branch flow path 16 forms a bed of silica gel and comprises a 6.35 mm diameter stainless steel tube packed with silica gel, approximately 25 cm. in length. Branch flow path 16 is connected to ports 28 and 30 of block valves 18 and 20 by a pair of face seal fittings 32 and 34 fitted with filter gaskets.

The silica gel used in branch flow path 16 comprises 40–60 mesh grade-12 silica gel chromatography packing material. The silica gel must first be dried in a backflow of gas. To this end, three-way valves 18 and 20 are first set so that ports 24, 26 and 30 are open while port 28 is closed. Face seal fitting 32 is loosened to allow the backflow of gas to escape from flow circuit 12. A flow of ultra-high purity nitrogen containing below about 1.0 ppb moisture is then induced through the bed formed in branch flow path 16. The source of ultra-high purity nitrogen is connected to an inlet port 35 of three-way valve 18 by a face seal fitting 36 in order to create the backflow. A restriction 38 is placed upon an outlet 40 of atmospheric pressure ionization mass spectrometry system 42 to maintain the pressure within the apparatus 10 above atmospheric pressure. It should be noted that a forward flow rather than a back flow can be used in the drying stage although possibly at reduced efficiency. An inlet 44 of atmospheric pressure ionization mass spectrometry system 42 is connected to an outlet port 46 of three-way valve 20 by a face seal fitting 48. During the back flow period, branch flow path 16 is also heated by wrapping branch path 16 with heating tape and alumina insulation. A thermocouple and digital temperature controller can be used to control power input to the heating tape.

After the bed of silica gel is dried, face seal fitting 32 is tightened while the first and second three-way valves 18 and 20 are set to close ports 24, 28, 26, and 30 thereof. At the same time face seal fitting 36 is connected to the gas to be sampled. Thereafter, in order to then analyze the gas for trace impurities, three-way valves 18 and 20 are set to open ports 28 and 30, while closing ports 24 and 26. The gas then flows to system 42 through an inlet 44 connected to outlet port 46 of three-way valve 20 by a face seal fitting 48. In order to measure the moisture content within the gas sample to be analyzed, three-way valves 18 and 20 can be reset to close ports 28 and 30, while opening ports 24 and 26. As can be appreciated, the use of the three-way valves and the face seal fittings in the manner outlined above for both drying the silica gel and for performing the analysis, environmentally isolate the silica gel, that is, prevent the silica gel from being exposed to air which in itself contains moisture or any other source of environmental moisture.

As an example, branch flow path 16 can be baked at about 150° C. for approximately one hour while a back flow house nitrogen is induced within branch flow path 16 at a flow rate of about 0.8 liters per minute. When a gas sample to be analyzed is subsequently passed through the bed of silica gel, the moisture level can be decreased to approximately 1.07 parts per billion. If the bed of silica gel is baked at approximately 200° C. for 4½ hours, the moisture content of the bed can be reduced to approximately 100 parts per trillion.

While the invention has been described with reference to a preferred embodiment, it will readily be understood by those skilled in the art that numerous additions, omissions and changes can be made without departing from the spirit and scope of the invention.

We claim:

1. In a method of analyzing a gas sample for trace impurity concentration by atmospheric pressure ionization mass spectroscopy, the improvement comprising:
   removing moisture without removing the trace impurity from the gas sample before analyzing the gas sample by passing the gas sample through a bed of silica gel; and
   before passing the gas sample through the bed of silica gel, sufficiently drying the bed of silica gel so that remaining moisture present in the gas sample after passage through the bed of silica gel is at a sufficiently low concentration such that the trace impurity concentration as analyzed by atmospheric pressure ionization mass spectroscopy is not effected by the remaining moisture.

2. The improvement of claim 1, wherein the bed of silica gel is dried by introducing a gas flow through the bed of silica gel while heating the bed of silica gel, the gas flow having an ultra-high purity and being chemically non-reactive with the silica gel.

3. The method of claim 2 wherein the bed of silica gel is heated at about 200° C. for about 4.5 hours.

* * * * *